(12) United States Patent
Teles et al.

(10) Patent No.: US 7,754,172 B2
(45) Date of Patent: *Jul. 13, 2010

(54) METHOD FOR ISOLATING $N_2O$

(75) Inventors: Joaquim Henrique Teles, Otterstadt (DE); Beatrice Roessler, Bad Duerkheim (DE); Dieter Baumann, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/094,731

(22) PCT Filed: Nov. 21, 2006

(86) PCT No.: PCT/EP2006/068714

§ 371 (c)(1),
(2), (4) Date: May 22, 2008

(87) PCT Pub. No.: WO2007/060160

PCT Pub. Date: May 31, 2007

(65) Prior Publication Data

US 2008/0274032 A1  Nov. 6, 2008

(30) Foreign Application Priority Data

Nov. 22, 2005  (DE) .................. 10 2005 055 588

(51) Int. Cl.
  *B01D 53/56* (2006.01)
  *C01B 21/22* (2006.01)
(52) U.S. Cl. .................. 423/235; 423/219; 423/400; 95/149; 95/199; 95/223; 95/232
(58) Field of Classification Search .................. 423/219, 423/235, 400; 95/149, 199, 223, 232
See application file for complete search history.

(56) References Cited

U.S. PATENT DOCUMENTS

| | | | |
|---|---|---|---|
| 3,650,695 A * | 3/1972 | Bogdan et al. .............. 423/613 |
| 3,656,899 A | 4/1972 | Baechle et al. | |
| 4,139,595 A * | 2/1979 | Vaseen .................. 423/393 |
| 4,177,645 A | 12/1979 | Schwarz | |
| 4,230,533 A * | 10/1980 | Giroux .................. 203/1 |
| 4,844,715 A | 7/1989 | Henrich et al. | |
| 5,401,884 A | 3/1995 | Diercks et al. | |
| 5,849,257 A | 12/1998 | Fujiwara et al. | |
| 6,080,226 A | 6/2000 | Dolan et al. | |
| 6,370,911 B1 | 4/2002 | Zhou et al. | |
| 6,387,161 B1 | 5/2002 | Zhou et al. | |
| 6,505,482 B2 | 1/2003 | Zhou et al. | |
| 7,105,704 B2 | 9/2006 | Panov et al. | |
| 7,282,612 B2 | 10/2007 | Panov et al. | |
| 2005/0203316 A1 | 9/2005 | Panov et al. | |
| 2006/0281952 A1 | 12/2006 | Teles et al. | |
| 2008/0274032 A1 * | 11/2008 | Teles et al. .................. 423/405 |

FOREIGN PATENT DOCUMENTS

| | | |
|---|---|---|
| DE | 2040219 | 3/1971 |
| DE | 2732267 | 1/1979 |
| DE | 19605211 | 8/1997 |
| DE | 102004046167 | 4/2006 |
| EP | 0624565 | 11/1994 |
| EP | 1076217 | 2/2001 |
| GB | 649680 | 1/1951 |
| GB | 1327401 | 8/1973 |
| WO | 98/25698 | 6/1998 |
| WO | 00/01654 | 1/2000 |
| WO | 00/73202 | 7/2000 |
| WO | 03/078370 | 9/2003 |
| WO | 03/078371 | 9/2003 |
| WO | 03/078372 | 9/2003 |
| WO | 03/078374 | 9/2003 |
| WO | 03/078375 | 9/2003 |
| WO | 04/000777 | 12/2003 |
| WO | 2004/096745 | 11/2004 |
| WO | 2005/030689 | 4/2005 |
| WO | 2005/030690 | 4/2005 |
| WO | 2006/032502 | 3/2006 |

OTHER PUBLICATIONS

A.S. Noskov et al., "Ammonia oxidation into nitrous oxide over Mn/Bi/Al catalyst I. Single cooling tube experiments", Chemical Engineering Journal 91 (2003), pp. 235-242.

(Continued)

*Primary Examiner*—Scott Kastler
*Assistant Examiner*—Brian Walck
(74) *Attorney, Agent, or Firm*—Oblon, Spivak, McClelland, Maier & Neustadt, L.L.P.

(57) ABSTRACT

The present invention relates to a process for purifying a gas mixture G-0 comprising dinitrogen monoxide, at least comprising the absorption of the gas mixture G-0 in an organic solvent, subsequent desorption of a gas mixture G-1 from the laden organic solvent, absorption of the gas mixture G-1 in water and subsequent desorption of a gas mixture G-2 from the laden water, and also to the use of a purified gas mixture which comprises dinitrogen monoxide and is obtainable by such a process as an oxidizing agent for olefins.

19 Claims, No Drawings

OTHER PUBLICATIONS

Gennady I. Panov et al., "Non-catalytic liquid phase oxidation of alkenes with nitrous oxide. 1. Oxidation of cyclohexene to cyclohexanone", React.Kinet. Catal. Lett., vol. 76, No. 2, pp. 401-406, 2002.

Konstatin A. Dubkov et al., "Non-catalytic liquid phase oxidation of alkenes with nitrous oxide. 2. Oxidation of cyclopentene to cyclopentanone", React. Kinet. Catal. Lett., vol. 77, No. 1, 2002, pp. 197-205.

E. V. Starokon et al., "Liquid phase oxidation of alkenes with nitrous oxide to carbonyl compounds", Adv. Synth. Catal., 2004, 346, pp. 268-274.

Anthony K. Uriarte, "Nitrous oxide ($N_2O$)—Waste to Value", Studies in Surface Science and Catalysis 130 A. Corma, F.V. Melo, S. Mendioroz and J.L.G. Fierro (Editors), 2000.

M. Thiemann et al., "Nitric Acid, Nitrous Acid, and Nitrogen Oxides to Nuclear Technology", Ullmann's Encyclopedia of Industrial Chemistry, $6^{tth}$ Edition, 2000, vol. 23, Electronic Edition, Chapter, Section 1.4.2.3.

J. Wolf et al., "Catalytic Reduction of Nitrogen Oxides in Flue Gases and Process off-Gases", Ullmann's Encyclopedia of Industrial Chemistry, vol. 1., $6^{th}$ Edition, 2000, Section 7.2.3.1v.

\* cited by examiner

METHOD FOR ISOLATING N$_2$O

The present invention relates to a process for purifying a gas mixture G-0 comprising dinitrogen monoxide, and to the use of a purified gas mixture which comprises dinitrogen monoxide and is obtainable by such a process as an oxidizing agent for olefins.

The prior art discloses various preparation processes for dinitrogen monoxide. It is likewise known that dinitrogen monoxide can be used, for example, as an oxidizing agent for olefins.

For instance, WO 98/25698 discloses a process for preparing dinitrogen monoxide by catalytic partial oxidation of NH$_3$ with oxygen. According to WO 98/25698, a catalyst composed of manganese oxide, bismuth oxide and aluminum oxide is used, which leads to dinitrogen monoxide with high selectivity. A similar catalyst system is also described in detail in a scientific study (Noskov et al., *Chem. Eng. J.* 91 (2003) 235-242). U.S. Pat. No. 5,849,257 likewise discloses a process for preparing dinitrogen monoxide by oxidation of ammonia. The oxidation takes place in the presence of a copper-manganese oxide catalyst.

In the process disclosed in WO 00/01654, dinitrogen monoxide is prepared by reducing a gas stream comprising NO$_x$ and ammonia.

The oxidation of an olefinic compound to an aldehyde or a ketone by means of dinitrogen monoxide is described, for example, in GB 649,680 or the equivalent U.S. Pat. No. 2,636,898. Both documents quite generally disclose that the oxidation can in principle be effected in the presence of a suitable oxidation catalyst.

The more recent scientific articles of G. L. Panov et al., "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. Vol. 77, No. 1 (2002) p. 197-205 likewise describe oxidations of olefinic compounds with dinitrogen monoxide. A scientific article "Liquid Phase Oxidation of Alkenes with Nitrous Oxide to Carbonyl Compounds" by E. V. Starokon et al. in *Adv. Synth. Catal.* 2004, 346, 268-274 also includes a mechanistic study of the oxidation of alkenes with dinitrogen monoxide in the liquid phase.

The synthesis of carbonyl compounds from alkenes with dinitrogen monoxide is also described in various international patent applications. For instance, WO 03/078370 discloses a process for preparing carbonyl compounds from aliphatic alkenes with dinitrogen monoxide. The reaction is carried out at temperatures in the range from 20 to 350° C. and pressures of from 0.01 to 100 atm. WO 03/078374 discloses a corresponding process for preparing cyclohexanone. According to WO 03/078372, cyclic ketones having from 4 to 5 carbon atoms are prepared. According to WO 03/078375, cyclic ketones are prepared under these process conditions from cyclic alkenes having from 7 to 20 carbon atoms. WO 03/078371 discloses a process for preparing substituted ketones from substituted alkenes. WO 04/000777 discloses a process for reacting di- and polyalkenes with dinitrogen monoxide to give the corresponding carbonyl compounds. The purification of dinitrogen monoxide is not mentioned in these documents.

It is likewise known that offgas streams comprising dinitrogen monoxide can be used for further reactions. Dinitrogen monoxide is obtained as an undesired by-product in various chemical processes, especially in oxidations with nitric acid and there very particularly in the oxidation of cyclohexanone and/or cyclohexanol to adipic acid. Other examples of processes in which dinitrogen monoxide is obtained as an undesired by-product are the oxidation of cyclododecanone and/or cyclododecanol with nitric acid to give dodecanedicarboxylic acid and the partial oxidation of NH$_3$ to NO.

For instance, WO 2005/030690, WO 2005/030689 and WO 2004/096745 disclose processes for oxidizing olefins with dinitrogen monoxide, specifically the oxidation of cyclododecatriene, of cyclododecene and of cyclopentene. All three applications disclose that, in addition to other dinitrogen monoxide sources, it is also possible to use offgas streams which can be purified, for example, by distillative methods before they are used as oxidizing agents.

Both in the preparation of dinitrogen monoxide and in the use of offgas streams, N$_2$O is obtained initially as a dilute gaseous mixture with other components. These components can be divided into those which have a disruptive effect for specific applications and those which behave inertly. For use as an oxidizing agent, gases having a disruptive effect include NO$_x$ or, for example, oxygen. The term "NO$_x$", as understood in the context of the present invention, refers to all compounds N$_a$O$_b$ where a is 1 or 2 and b is a number from 1 to 6, except N$_2$O. Instead of the term "NO$_x$", the term "nitrogen oxides" is also used in the context of the present invention. Disruptive secondary components also include NH$_3$ and organic acids.

For specific applications, it is necessary to purify the dinitrogen monoxide used before the reaction. For example, for the use of dinitrogen monoxide as an oxidizing agent, it is necessary to remove disruptive secondary components such as oxygen or nitrogen oxides NO$_x$.

Processes for removing NO$_x$ are known in principle from the prior art. A review is given, for example, by M. Thiemann et. al in Ullmann's Encyclopedia, 6th Edition, 2000, Electronic Edition, Chapter "Nitric Acid, Nitrous Acid, and Nitrogen Oxides", Section 1.4.2.3.

The application WO 00/73202 describes a method as to how NO$_x$ and O$_2$ can be removed from an N$_2$O-containing gas stream. The NO$_x$ is removed by catalytic reduction with NH$_3$ and oxygen by catalytic reduction with hydrogen or other reducing agents. However, this method has the disadvantage that the product is contaminated with NH$_3$. A high depletion of oxygen, for example to more than 90% of the original amount, is possible only when a loss of N$_2$O is accepted, for example of from 3 to 5% of the amount originally present.

For specific applications, it may be necessary also to remove the inert compounds, since they can slow the desired reaction with N$_2$O by dilution. The term "inert gas", as used in the context of the present invention, refers to a gas which behaves inertly with regard to the reaction of N$_2$O with an olefin, i.e. reacts under the conditions of the reaction of olefins with N$_2$O neither with the olefins nor with N$_2$O. Inert gases include, for example, nitrogen, carbon dioxide, carbon monoxide, hydrogen, argon, methane, ethane and propane. However, the inert gases can lower the space-time yield, so that a depletion can likewise be advantageous. However, it may likewise be advantageous to obtain a gas mixture which still comprises inert gases and then can be used directly in a further reaction.

DE 27 32 267 A1 discloses, for example, a process for purifying dinitrogen monoxide, wherein nitrogen oxide, nitrogen dioxide, carbon dioxide and water are initially removed and the gas mixture is subsequently liquefied by compression to from 40 to 300 bar and cooling to from 0 to −88° C. From this liquefied gas mixture, dinitrogen monoxide is then removed. Although this method achieves a purification and concentration of the $N_2O$, it is economically unattractive owing to the required high pressure (60 bar), the low temperatures (−85° C.) and the associated high capital costs.

U.S. Pat. No. 4,177,645 discloses a process for removing dinitrogen monoxide from offgas streams which likewise comprises a prepurification and a low temperature distillation. The application EP 1 076 217 A1 likewise describes a method for removing low-boiling impurities from $N_2O$ by low temperature distillation.

U.S. Pat. Nos. 6,505,482, 6,370,911 and 6,387,161 also disclose processes for purifying dinitrogen monoxide, in which a low temperature distillation is in each case carried out in a special plant.

However, as a result of the high pressures and low temperatures, a low temperature distillation entails high apparatus demands, which make the purification of the dinitrogen monoxide with such a process inconvenient and costly. Particularly troublesome in this context is the fact that the melting point of $N_2O$ at standard pressure is only 3 K below the boiling point. It is therefore necessary to employ high pressures.

DT 20 40 219 discloses a preparation process for dinitrogen monoxide, wherein the dinitrogen monoxide obtained is concentrated and purified after the synthesis. According to DT 20 40 219, dinitrogen monoxide is prepared initially by oxidizing ammonia. The dinitrogen monoxide prepared is purified by separating the oxidized gases and concentrating by absorption under high pressure, which is followed by a desorption under reduced pressure. Secondary components are removed, for example, by treatment with an alkali solution. According to DT 20 40 219, water is used as the solvent for the absorption of the gas mixture.

It is possible with the process disclosed in DT 20 40 219 to separate the different nitrogen oxides, but the process entails the use of large amounts of solvent and/or high pressures for the absorption owing to the comparatively low solubility of $N_2O$ in water.

DE 10 2004 046167.8 discloses a process for purifying a gas mixture comprising dinitrogen monoxide, which comprises at least one absorption of the gas mixture in an organic solvent and subsequent desorption of the gas mixture from the laden organic solvent, and also the adjustment of the content of nitrogen oxides $NO_x$ in the gas mixture to at most 0.5% by volume based on the total volume of the gas mixture. DE 10 2004 046167.8 also discloses that the process may comprise a plurality of absorption and desorption steps. DE 10 2004 046167.8 discloses only organic solvents as the absorption medium.

Starting from this prior art, it was an object of the present invention to provide a safe process with which dinitrogen monoxide-containing streams can be purified and concentrated in an effective and inexpensive manner. Dinitrogen monoxide purified in this way is required in particular as an oxidizing agent. It was a further object of the present invention to provide processes for preparing gas mixtures which can be used as an oxidizing agent without further treatment or addition of other inertizing agents.

According to the invention, this object is achieved by a process for purifying a gas mixture G-0 comprising dinitrogen monoxide, at least comprising the following steps:

A1 absorption of the gas mixture G-0 in an organic solvent
A2 desorption of a gas mixture G-1 from the laden organic solvent
B1 absorption of the gas mixture G-1 in water
B2 desorption of a gas mixture G-2 from the laden water.

One advantage of the process according to the invention is that, in addition to the troublesome components, some of the inert components are also removed. The dinitrogen monoxide purified in accordance with the invention is thus simultaneously concentrated.

According to the invention, the gas mixture G-1 has a higher content of dinitrogen monoxide than the gas mixture G-0. According to the invention, the gas mixture G-2 in turn has a higher content of dinitrogen monoxide than the gas mixture G-1.

Moreover, the process according to the invention has the advantage that, in the second absorption, i.e. at a higher content of dinitrogen monoxide, water is used as the absorbent. This avoids the contacting of dinitrogen monoxide as a strong oxidizing agent in high concentrations with an organic solvent, which would lead to a high level of apparatus demands and high costs. The inventive use of water as the solvent in the second absorption and desorption in step B1 and B2 additionally prevents the gas mixture G-2 from becoming contaminated with organic solvent, which would lead to further purification steps.

The use of a two-stage absorption/desorption with an organic solvent in step A1 and A2 and water in step B1 and B2 has the advantage, in particular, that the first stage utilizes the high solubility of $N_2O$ in organic solvents in order to achieve high concentration factors with smaller apparatus and lower circulation. After the first absorption/desorption, the gas mixture G-1 already has an $N_2O$ concentration which makes it advantageous to use water as the solvent in the absorption/desorption for safety reasons. In spite of this, the higher $N_2O$ concentration in the second stage enables the use of smaller apparatus.

Dinitrogen monoxide purified in this way can be used advantageously as the oxidizing agent especially in liquid form. Advantageously, the gas mixture G-2 may also comprise carbon dioxide in addition to dinitrogen monoxide. $CO_2$ has an inertizing action and ensures safe operation in the course of preparation and especially in the course of storage and further use of the gas mixture G-2 comprising dinitrogen monoxide. It has been found that, in the presence of $CO_2$ as an inert gas in gas mixtures comprising $N_2O$ in comparison to other inert gases, distinctly smaller amounts of carbon dioxide are required to suppress the self-decomposition tendency of dinitrogen monoxide. Thus, small amounts of $CO_2$ are sufficient for inertization.

According to the invention, the gas mixture G-0 comprising dinitrogen monoxide used may in principle stem from any source.

The term "gas mixture" herein refers to a mixture of two or more compounds which are in the gaseous state at ambient pressure and ambient temperature. At altered temperature or altered pressure, the gas mixture may also be present in another state of matter, for example liquid, and is still referred to as a gas mixture in the context of the present invention.

When a gas mixture G-0 is used, its content of dinitrogen monoxide is substantially arbitrary, as long as it is guaranteed that the inventive purification is possible.

The $N_2O$-containing gas mixtures which are used as gas mixture G-0 for this process generally have an $N_2O$ content between 2 and 80% by volume of $N_2O$. It also comprises, for example, from 2 to 21% by volume of $O_2$ and up to 30% by volume of $NO_x$ as undesired components. In addition, it may also comprise varying amounts of $N_2$, $H_2$, $CO_2$, $CO$, $H_2O$, $NH_3$; traces of nitric acid and organic compounds may also be present.

In the context of the present invention, the composition of the gas mixtures or of the liquefied gas mixtures is specified in % by volume. The data relate to the composition of the gas mixtures at ambient pressure and ambient temperature.

In a preferred embodiment of the process according to the invention, a gas mixture G-0 comprising at least 3% by volume of dinitrogen monoxide is used, but preference is given in turn to using mixtures having a dinitrogen monoxide content in the range from 4 to 60% by volume, more preferably in the range from 5 to 25% by volume and especially preferably in the range from 8 to 14% by volume.

In principle, the composition of the mixtures may be determined in the context of the present invention in any way known to those skilled in the art. The composition of the gas mixtures is determined in the context of the present invention preferably by gas chromatography. However, it may also be determined by means of UV spectroscopy, IR spectroscopy or by wet chemical methods.

In a preferred embodiment of the present invention, the gas mixture G-0 comprising dinitrogen monoxide is at least one dinitrogen monoxide-containing offgas of a chemical process. The scope of the present invention also embraces embodiments in which at least two nitrogen monoxide-containing offgases of a single plant serve as the gas mixture comprising dinitrogen monoxide. Equally embraced are embodiments in which at least one dinitrogen monoxide-containing offgas of one plant and at least one further dinitrogen monoxide-containing offgas of at least one further plant serve as the gas mixture comprising dinitrogen monoxide.

Accordingly, the present invention also relates to a process as described above, wherein the gas mixture comprising dinitrogen monoxide is at least one dinitrogen monoxide-containing offgas of at least one industrial process.

The term "gas mixture comprising dinitrogen monoxide" refers in the context of the present invention both to embodiments in which the offgas mentioned is subjected to the inventive purification process in unmodified form and to embodiments in which at least one of the offgases mentioned is subjected to a modification.

The term "modification" as used in this context within the scope of the present invention refers to any suitable process by which the chemical composition of a gas mixture is altered. Accordingly, the term "modification" comprises, inter alia, embodiments in which a dinitrogen monoxide-containing offgas is concentrated with regard to the dinitrogen monoxide content in at least one suitable process. Preference is given to not subjecting the offgas to any modification.

In a further embodiment, the chemical composition of an offgas may also be altered by adding pure dinitrogen monoxide to the offgas.

The gas mixture G-0 comprising $N_2O$ which is used may, for example, be an offgas from an industrial process. It preferably stems from an offgas of a plant for preparing carboxylic acids by oxidation of alcohols or ketones with nitric acid, for example from an adipic acid or dodecanedicarboxylic acid plant, from the offgas of a nitric acid plant which uses the above offgas streams as a reactant, from the offgas of a plant for the partial oxidation of $NH_3$ or from the offgas of a plant which uses the gas mixtures generated therein, for example a hydroxylamine plant.

According to the invention, it is also possible to use a mixture of different offgases.

In a more preferred embodiment of the present invention, the at least one dinitrogen monoxide-containing offgas stems from an adipic acid plant, a dodecanedicarboxylic acid plant, a hydroxylamine plant and/or a nitric acid plant, the latter in turn preferably being operated with at least one offgas of an adipic acid plant, of a dodecanedicarboxylic acid plant or of a hydroxylamine plant.

In a preferred embodiment, the offgas stream of an adipic acid plant is used, in which generally from 0.8 to 1.0 mol of $N_2O$ is formed per mole of adipic acid formed by oxidation of cyclohexanol/cyclohexanone mixtures with nitric acid. As described, for example, in A. K. Uriarte et al., Stud. Surf. Sci. Catal. 130 (2000) p. 743-748, the offgases of adipic acid plants also comprise different concentrations of further constituents including nitrogen, oxygen, carbon dioxide, carbon monoxide, nitrogen oxides, water and volatile organic compounds.

The abovementioned dodecanedicarboxylic acid plant is substantially of an identical plant type.

An example of a typical composition of an offgas of an adipic acid plant or of a dodecanedicarboxylic acid plant is reproduced in the following table:

| Component | Concentrations/% by wt. |
| --- | --- |
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of an adipic acid plant or of a dodecanedicarboxylic acid plant may be used directly in the process according to the invention.

In a likewise preferred embodiment, the offgas stream of a nitric acid plant is used which is fed fully or partly with offgases comprising dinitrogen monoxide and nitrogen oxides from other processes. In such nitric acid plants, nitrogen oxides are adsorbed and for the most part converted to nitric acid, while dinitrogen monoxide is not converted. For example, such a nitric acid plant may be supplied by nitrogen oxides which are prepared by selective combustion of ammonia and by offgases of an adipic acid plant and/or by offgases of a dodecanedicarboxylic acid plant. It is equally possible to supply such a nitric acid plant solely by offgases of an adipic acid plant and/or by offgases of a dodecanedicarboxylic acid plant.

The offgases of such nitric acid plants always comprise varying concentrations of still further constituents including nitrogen, oxygen, carbon dioxide, carbon monoxide, nitrogen oxides, water and volatile organic compounds.

An example of a typical composition of an offgas of such a nitric acid plant is reproduced in the following table:

| Component | Concentrations/% by wt. |
| --- | --- |
| $NO_x$ | <0.1 |
| $N_2O$ | 4-36 |
| $N_2$ | 57-86 |
| $O_2$ | 3-9 |
| $CO_2$ | 1-4 |
| $H_2O$ | ~0.6 |

The offgas stream of a nitric acid plant may be used directly in the process according to the invention.

In a likewise preferred embodiment of the process according to the invention, the offgas stream of a hydroxylamine plant is used, in which, for example, ammonia is initially oxidized with air or oxygen to give NO, and small amounts of dinitrogen monoxide are formed as a by-product. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant comprises dinitrogen monoxide in the range from 9 to 13% by volume in hydrogen. This purge stream may be used as such for the inventive purification. It is equally possible to concentrate this stream in a suitable manner with regard to the dinitrogen monoxide content as described above.

Accordingly, the present invention also relates to a process as described above, wherein the gas mixture comprising dinitrogen monoxide is the offgas of an adipic acid plant and/or of a dodecanedicarboxylic acid plant and/or of a hydroxylamine plant and/or of a nitric acid plant operated with the offgas of an adipic acid plant and/or of a dodecanedicarboxylic acid plant and/or of a hydroxylamine plant.

It is equally possible in the context of the process according to the invention to selectively prepare dinitrogen monoxide for use in the process. Preference is given inter alia to the preparation via the thermal decomposition of $NH_4NO_3$, as described, for example, in U.S. Pat. No. 3,656,899, whose contents on this subject are incorporated by reference fully into the context of the present application. Preference is likewise further given to the preparation via the catalytic oxidation of ammonia, as described, for example, in U.S. Pat. No. 5,849,257 or in WO 98/25698, whose contents on this subject are incorporated by reference fully into the context of the present application.

The gas mixture G-2 obtained by the purification process according to the invention comprises at least 50% by volume of $N_2O$, more preferably at least 60% by volume of $N_2O$ and most preferably at least 75% by volume of $N_2O$. The gas mixture G-2 comprises typically up to 99% by volume of $N_2O$, in particular up to 97% by volume of $N_2O$, for example up to 96% by volume of $N_2O$, up to 95% by volume of $N_2O$, up to 94% by volume of $N_2O$, up to 93% by volume of $N_2O$, up to 92% by volume of $N_2O$, up to 91% by volume of $N_2O$, up to 90% by volume of $N_2O$ or even up to 85% by volume of $N_2O$.

At the same time, the gas mixture G-2 comprises less than 1% by volume of $O_2$, in particular less than 0.5% by volume of $O_2$, less than 0.5% by volume of $NO_x$ and less than 1% by volume of $NH_3$.

The gas mixture G-2 obtained by the purification process according to the invention comprises from 5 to 20% by volume of $CO_2$, more preferably from 6 to 18% by volume of $CO_2$ and most preferably from 8 to 12% by volume of $CO_2$.

According to the invention, the $N_2O$ is concentrated by a first selective absorption of $N_2O$ and thus preferably, owing to the similar physical properties, also of $CO_2$ from the gas mixture G-0 in a suitable organic solvent and subsequent desorption of the gas mixture G-1 from the laden solvent in step A1 and step A2. According to the invention, the gas mixture G-1 is absorbed in step B1 for a further concentration in water. In the desorption in step B2, the gas mixture G-2 is obtained in accordance with the invention.

Suitable solvents for the absorption in step A1 are those which have a better solubility for $N_2O$ and preferably also $CO_2$ as inert component than for the undesired components of the entering reactant gas G-0.

According to the invention, the organic solvents used may be any solvents in which the ratio between $N_2O$ solubility (in mol/mol of solvent) and the solubility of the undesired secondary components under the conditions prevailing in the absorber (this ratio is referred to hereinbelow as γ) is at least 5. This ratio may be determined for each individual component present in the gas mixture. Preferred organic solvents have, for example at 30° C., a $\gamma_{O2}$ value of from 6 to 30, preferably from 9 to 25, and a $\gamma_{N2}$ value of greater than 10, preferably of greater than 15, in particular of greater than 20.

Examples of suitable solvents are, for example, aliphatic hydrocarbons, preferably having at least 5 carbon atoms, more preferably having at least 8 carbon atoms, substituted or unsubstituted aromatic hydrocarbons, esters, ethers, amides, lactones, lactams, nitriles, alkyl halides, olefins or mixtures of these solvents.

According to the invention, very particular preference is given to solvents which have a boiling point at standard pressure of at least 100° C., since this reduces the solvent losses both in the offgas stream of the absorber and of the desorber.

In addition, solvents suitable in accordance with the invention simultaneously have a good solubility for dinitrogen monoxide. The solubility is specified by the ratio between the partial pressure of $N_2O$ in the gas phase and the molar proportion of $N_2O$ in the liquid phase (Henry coefficient, $H_{N2O}$), i.e. a small value means a high solubility of dinitrogen monoxide in the solvent. This ratio for an organic solvent used in particular in the first step at 30° C. is preferably less than 1000, more preferably less than 750, particularly preferably less than 500, in particular less than 150.

Suitable solvents include N-methylpyrrolidone, dimethylformamide, dimethyl sulfoxide, propylene carbonate, sulfolane, N,N-dimethylacetamide or cyclopentane. Particular preference is given in the context of the present invention, for example, to toluene, nitrobenzene, 1,2-dichlorobenzene, tetradecane, for example a technical-grade mixture of saturated hydrocarbons having predominantly 14 carbon atoms, and dimethyl phthalate.

In a preferred embodiment, the present invention therefore relates to a process for purifying a gas mixture comprising dinitrogen monoxide as described above, wherein the organic solvent is selected from the group consisting of toluene, nitrobenzene, 1,2-dichlorobenzene, tetradecane and dimethyl phthalate.

In the context of the present invention, the gas mixture G-1 has, for example, a content of $N_2O$ of from 50 to 80% by volume, preferably from 55 to 75% by volume, in particular from 58 to 70% by volume, more preferably, for example, 59% by volume, 60% by volume, 61% by volume, 62% by volume, 63% by volume, 64% by volume, 65% by volume, 66% by volume, 67% by volume, 68% by volume or 69% by volume.

The gas mixture G-1 has, for example, a content of $CO_2$ of from 5 to 15% by volume, preferably of from 6 to 12% by volume, more preferably, for example, 7% by volume, 9% by volume, 10% by volume or 11% by volume. At the same time, the gas mixture G-1 has, for example, a content of $O_2$ of from 1.0 to 3.0% by volume, preferably of from 1.5 to 2.5% by volume, more preferably, for example, 1.1% by volume, 1.2% by volume, 1.3% by volume, 1.4% by volume, 1.5% by volume, 1.6% by volume, 1.7% by volume, 1.8% by volume, 1.9% by volume, 2.0% by volume, 2.1% by volume, 2.2% by volume, 2.3% by volume or 2.4% by volume. In addition, the gas mixture G-1 may comprise from 20 to 40% by volume of $N_2$, preferably from 20 to 35% by volume, and also further components, for example nitrogen oxides or solvent residues. The sum of the components of the gas mixture G-1 adds up to 100% by volume.

In step B1 and B2, an absorption/desorption is effected with water as the solvent. Water has a high selectivity for the components desired, especially dinitrogen monoxide and carbon dioxide. At the same time, the absolute solubility of dinitrogen monoxide in water is sufficient to achieve further concentration. Water as the solvent has the advantage that, even under pressure in the presence of concentrated dinitrogen monoxide, no safety problems occur. At the same time, no contamination of the gas mixture G-2 with an organic solvent can occur, which would necessitate additional purification steps.

In the context of the present invention, the gas mixture G-2 has, for example, a content of $N_2O$ of from 70 to 95% by volume, preferably of from 75 to 90% by volume, in particular of from 80 to 85% by volume, more preferably, for example, 81% by volume, 82% by volume, 83% by volume or 84% by volume.

The gas mixture G-2 has, for example, a content of $CO_2$ of from 1 to 20% by volume, preferably of from 5 to 15% by volume, more preferably, for example, 6% by volume, 7% by volume, 8% by volume, 9% by volume, 10% by volume, 11% by volume, 12% by volume, 13% by volume or 14% by volume. At the same time, the gas mixture G-2 has, for example, a content of $O_2$ of from 0.01 to 5.0% by volume, preferably of from 0.1 to 2.5% by volume, more preferably, for example, from 0.2 to 1.0% by volume. In addition, the gas mixture G-2 may comprise from 0.1 to 10% by volume of $N_2$, preferably from 0.5 to 5% by volume, and also further components, for example nitrogen oxides or solvent residues. The sum of the components of the gas mixture G-2 adds up to 100% by volume.

The absorption in step A1 or B1 of the process according to the invention can in principle be effected by all processes known to those skilled in the art. In particular, the absorption of $N_2O$ in the solvent can be brought about by increasing the pressure of the reactant gas or by lowering the temperature of the solvent or by a combination of the measures mentioned. In the context of the present application, solvents are understood to mean both water and organic solvents.

In the absorption, the gas mixture is preferably initially compressed, for example to a pressure of from 10 to 35 bar, preferably of from 15 to 30 bar, preferably of from 16 to 25 bar. Subsequently, the compressed gas mixture is preferably absorbed at this pressure in an organic solvent in step A1 or in water in step B1.

A preferred embodiment of the present invention therefore relates to a purification process as described above, wherein the pressure in the absorption in A1 or B1 is in a range of from 10 to 35 bar.

According to the invention, the absorption in step A1 and B1 is effected in devices (absorbers) in which a gas-liquid phase interface is generated, by means of which heat and mass transfer between the phases is enabled, and which, if required, are equipped with internal or external devices for heat supply and/or heat removal.

The phases can be conducted in the absorber in cocurrent, in countercurrent or a combination thereof.

According to the invention, the absorption can be carried out in one or more stages, preferably in one stage. In the absorption, the absorber used is preferably a device with a plurality of theoretical plates, in particular from 2 to 8 theoretical plates, more preferably from 3 to 6.

Possible embodiments of the absorber are columns having trays, for example bubble-cap trays or sieve trays, columns having structured internals, for example structured packings, columns having unstructured internals, for example random packings, or apparatus in which the liquid phase is present in dispersed form, for example by spraying in nozzles, or a combination thereof.

The desorption of $N_2O$ from the laden solvent in step A2 or B2 of the process according to the invention may be brought about by pressure reduction via the solvent, temperature increase of the solvent or by stripping with solvent vapor or a combination thereof.

The demands on the devices (desorbers) for the desorption of $N_2O$ from the laden solvent, and the conduction of the phases, are analogous to those of the absorber, i.e. suitable units are those in which a gas-liquid phase interface is generated, through which heat and mass transfer between the phases is enabled, and which are equipped if required with internal or external equipment for heat supply and/or heat removal.

According to the invention, the desorption may be carried out in one or more stages.

Possible embodiments of the desorber are a simple (flash) vessel and columns.

A preferred embodiment of the present invention in which the absorption and desorption are combined in one apparatus is, for example, the dividing wall column. In this column, the absorption and desorption are operated in countercurrent in several stages by temperature change, combined with a stripping with solvent vapor. In this context, an apparatus combination of absorption and desorption can be effected both in A1 and A2, and in B1 and B2, especially in a dividing wall column.

In a preferred embodiment, the present invention therefore relates to a process as described above, wherein steps A1 and A2, or steps B1 and B2, or steps A1 and A2 and steps B1 and B2 are carried out in a dividing wall column.

In a particularly preferred embodiment of the invention, in step A1, the gas mixture G-0 comprising $N_2O$ is initially absorbed under elevated pressure $p_{abso}$ in an absorption column operated in countercurrent and having random packing, and transferred in step A2 into a vessel in which the $N_2O$-laden solvent is decompressed to a lower pressure $p_{deso} < p_{abso}$. The process is preferably operated virtually isothermally with a temperature differential between absorption and desorption temperature of not more than 20K, preferably not more than 15K, in particular not more than 10K. The absorption pressure is from 1 to 100 bar, preferably from 5 to 65 bar, in particular from 10 to 40 bar, preferably from 10 to 35 bar, more preferably from 15 to 30 bar, further preferably from about 16 to 25 bar, and the desorption pressure from 0.1 to 2 bar, preferably from 0.5 to 1.5 bar, more preferably from 1.0 to 1.2 bar.

Preference is likewise given, in step B1, to first absorbing the gas mixture G-1 under elevated pressure $p_{abso}$ in an absorption column operated in countercurrent and having random packing, and transferring it in step B2 into a vessel in which the $N_2O$-laden water is decompressed to a lower pressure $p_{deso} < p_{abso}$. The process is preferably likewise operated virtually isothermally with a temperature differential between absorption and desorption temperature of not more than 20K, preferably not more than 15K, in particular not more than 10K. The absorption pressure is from 1 to 100 bar, preferably from 5 to 65 bar, in particular from 10 to 40 bar, preferably from 10 to 35 bar, more preferably from 16 to 30 bar, further preferably from about 20 to 25 bar, and the desorption pressure from 0.1 to 2 bar, preferably from 0.5 to 1.5 bar, more preferably from 1.0 to 1.2 bar.

In a further embodiment, the process according to the invention may further comprise a step C, wherein the content of nitrogen oxides in the gas mixture is adjusted to at most 0.5% by volume based on the total volume of the gas mixture.

The present invention therefore also relates to a process as described above, which additionally comprises the step of C adjusting the content of nitrogen oxides $NO_x$ in the gas mixture to at most 0.5% by volume based on the total volume of the gas mixture.

In the context of the present invention, step C may be carried out before or after steps A1, A2, B1 and B2. In one embodiment, the present invention therefore relates to a process as described above, wherein steps A1, A2, B1 and B2 are carried out before step C. In an alternative embodiment, the present invention relates to a process as described above, wherein step C is performed before steps A1, A2, B1 and B2.

When step C is carried out before steps A1, A2, B1 and B2, the $NO_x$ content is adjusted in the gas mixture G-0.

In this case, the gas mixture G-0 in the absorption in A1 preferably has an $N_2O$ content of from 4 to 25% by volume, preferably of from 6 to 20% by volume, in particular of from 8 to 18% by volume, more preferably, for example, 9% by volume, 10% by volume, 11% by volume, 12% by volume, 13% by volume, 14% by volume, 15% by volume, 16% by volume or 17% by volume.

The gas mixture has, for example, a content of $CO_2$ of from 0.1 to 7.5% by volume, preferably of from 0.5 to 5% by volume, more preferably from 1 to 2.5% by volume. At the same time, the gas mixture has, for example, a content of $O_2$ of from 1 to 10% by volume, preferably of from 2 to 7.5% by volume, more preferably, for example, from 3.0 to 6% by volume. Moreover, the gas mixture may comprise from 50 to 95% by volume of $N_2$, preferably from 60 to 90% by volume, more preferably from 70 to 85% by volume, and also further components, for example nitrogen oxides or solvent residues. $NO_x$ may be present, for example, in an amount of from 0 to 0.1% by volume, preferably from 0.0001 to 0.01% by volume, more preferably from 0.0005 to 0.05% by volume. The sum of the components of the gas mixture adds up to 100% by volume.

After the first absorption/desorption in A1 and A2 and before the second absorption/desorption in B1 and B2, the gas mixture preferably has an $N_2O$ content of from 40 to 80% by volume, preferably of from 50 to 75% by volume, in particular of from 55 to 70% by volume, more preferably, for example, 56% by volume, 57% by volume, 58% by volume, 59% by volume, 60% by volume, 61% by volume, 62% by volume, 63% by volume, 64% by volume, 65% by volume, 66% by volume, 67% by volume, 68% by volume or 69% by volume.

The gas mixture has, for example, a content of $CO_2$ of from 1 to 15% by volume, preferably of from 2 to 10% by volume, more preferably from 7 to 9% by volume. At the same time, the gas mixture has, for example, a content of $O_2$ of from 0.5 to 7.5% by volume, preferably of from 1 to 5% by volume, more preferably, for example, from 2.5 to 3.5% by volume. Moreover, the gas mixture may comprise from 5 to 40% by volume of $N_2$, preferably from 10 to 35% by volume, more preferably from 20 to 30% by volume, and also further components, for example nitrogen oxides or solvent residues. $NO_x$ may be present, for example, in an amount of from 0 to 0.1% by volume, preferably from 0.0001 to 0.01% by volume, more preferably from 0.0005 to 0.05% by volume. The sum of the components of the gas mixture adds up to 100% by volume.

After the second absorption/desorption in B1 and B2, the gas mixture preferably has an $N_2O$ content of from 60 to 95% by volume, preferably of from 70 to 90% by volume, in particular of from 75 to 85% by volume, more preferably, for example, 76% by volume, 77% by volume, 78% by volume, 79% by volume, 80% by volume, 81% by volume, 82% by volume, 83% by volume, 84% by volume or 85% by volume.

The gas mixture has, for example, a content of $CO_2$ of from 1 to 20% by volume, preferably of from 5 to 15% by volume, more preferably from 7.5 to 12.5% by volume. At the same time, the gas mixture has, for example, a content of $O_2$ of from 0.01 to 7.5% by volume, preferably of from 0.1 to 5% by volume, more preferably, for example, from 0.2 to 2.5% by volume. Moreover, the gas mixture may comprise from 0.1 to 10% by volume of $N_2$, preferably from 0.5 to 5% by volume, more preferably from 1 to 2.5% by volume, and also further components, for example nitrogen oxides or solvent residues. $NO_x$ may be present, for example, in an amount of from 0 to 0.1% by volume, preferably from 0.0001 to 0.01% by volume, more preferably from 0.0005 to 0.05% by volume. The sum of the components of the gas mixture adds up to 100% by volume.

When step C is carried out after steps A1, A2, B1 and B2, the gas mixture G-2 is treated.

After the second absorption/desorption in B1 and B2, and subsequent step C, the gas mixture preferably has an $N_2O$ content of from 60 to 95% by volume, preferably of from 70 to 90% by volume, in particular of from 75 to 85% by volume, more preferably, for example, 76% by volume, 77% by volume, 78% by volume, 79% by volume, 80% by volume, 81% by volume, 82% by volume, 83% by volume, 84% by volume or 85% by volume.

The gas mixture has, for example, a content of $CO_2$ of from 1 to 20% by volume, preferably of from 5 to 15% by volume, more preferably from 7.5 to 12.5% by volume. At the same time, the gas mixture has, for example, a content of $O_2$ of from 0.01 to 7.5% by volume, preferably of from 0.1 to 5% by volume, more preferably, for example, from 0.2 to 2.5% by volume. Moreover, the gas mixture may comprise from 0.1 to 10% by volume of $N_2$, preferably from 0.5 to 5% by volume, more preferably from 1 to 2.5% by volume, and also further components, for example nitrogen oxides or solvent residues. $NO_x$ may be present, for example, in an amount of from 0 to 0.1% by volume, preferably from 0.0001 to 0.01% by volume, more preferably from 0.0005 to 0.05% by volume. The sum of the components of the gas mixture adds up to 100% by volume.

In the context of the present invention, step C may also be carried out between steps A1 and A2 and steps B1 and B2. In this case, the gas mixture G-2 has approximately the same composition as the gas mixture which is obtained after the second absorption/desorption in B1 and B2 and subsequent step C.

It is equally possible in the context of the present invention that the process comprises a plurality of steps C. Thus, it is also possible, for example, to carry out a step C before steps A1, A2, B1 and B2, and a further step C after steps A1, A2, B1 and B2.

Accordingly, the present invention also relates to a process as described above, wherein step C is performed before steps A1, A2, B1 and B2.

In principle, all suitable processes for removing NO, are useful for step C of the process according to the invention. Suitable processes are, for example, the catalytic reduction with hydrocarbons or ammonia, the catalytic decomposition over suitable catalysts, absorption in strongly oxidizing solutions and the absorption in acidic or alkaline solutions.

Suitable oxidizing solutions in the context of the present invention are, for example, solutions of hydrogen peroxide. According to the invention, suitable strongly acidic solutions are, for example, solutions comprising nitric acid or sulfuric acid. According to the invention, suitable alkaline solutions are, for example, solutions comprising hydroxides or carbonates, for example sodium hydroxide or sodium carbonate.

Suitable liquids for this scrubbing, in addition to those already mentioned, are in particular those which are familiar to those skilled in the art for the removal of $NO_x$ from off-gases. Suitable scrubbing solutions or suspensions are, for example, aqueous solutions or suspensions comprising magnesium carbonate, magnesium hydroxide, solutions of vanadium in nitrous acid, ammonium sulfide and ammonium bisulfide, limewater, ammonia, hydrogen peroxide and in particular solutions comprising sodium carbonate, sodium bicarbonate or sodium hydroxide.

Suitable processes are specified, for example, in M. Thiemann et al. in Ullmann's Encyclopedia, 6th Edition, 2000, Electronic Edition, Chapter "Nitric Acid, Nitrous Acid, and Nitrogen Oxides", Section 1.4.2.3.

In general, the $NO_x$ absorption is effected in units in which a gas-liquid phase interface is present, through which mass and heat transfer between the phases is enabled, and which are equipped if required with internal or external equipment for heat supply and/or heat removal. The phases can be conducted in the absorber in cocurrent, in countercurrent or a combination thereof.

According to the invention, the absorption may be carried out in one or more stages.

According to the invention, the absorption is effected at temperatures between −20 and 100° C., preferably between 0 and 60° C., more preferably between 0 and 40° C., and at pressures between 0.1 and 100 bar, preferably between 1 and 30 bar.

Possible embodiments of the absorber are columns having trays, for example bubble-cap trays or sieve trays, columns having structured internals, for example structured packings, columns having unstructured internals, for example random packings, or apparatus in which the liquid phase is present in dispersed form, for example by spraying in nozzles, or a combination thereof.

In a further embodiment, the present invention therefore relates to a process as described above, wherein step C comprises the absorption of nitrogen oxides in acidic or alkaline solution.

In the context of the present invention, $NO_x$ can be removed by absorption in an acidic or an alkaline solution. The absorption is carried out between −20 and 120° C., in particular between −10 and 75° C., preferably between 0 and 60° C., for example between 0 and 40° C., and at a pressure between 0.2 and 100 bar, in particular between 0.5 and 50 bar, preferably between 1 and 10 bar.

When the $NO_x$ concentration in the $N_2O$-containing gas mixture is more than 1% by volume, the solvent used for step C is preferably aqueous nitric acid having an $HNO_3$ content between 0 and 69% by weight, preferably between 0 and 10% by weight. It is advantageous in this case that the $NO_x$ depletion in the gas phase is accompanied by the preparation of nitric acid with from 1 to 69% by weight of $HNO_3$. For the purposes of further utility, preference is given to preparing nitric acid having from 30 to 60% by weight of $HNO_3$.

In the context of the present invention, this procedure is used with preference, for example, when the $N_2O$-containing reactant gas stems from a carboxylic acid process (for example adipic acid), wherein $NO_x$ concentrations of from 1 to 50% by volume are present. The $NO_x$ removal in step C is in this case preferably carried out before the $N_2O$ concentration in step A1 and A2.

In one embodiment of the present invention, steps A1, A2, B1 and B2 may be followed by a further step C, preferably a chemical scrubbing, more preferably with sodium carbonate solution or sodium hydroxide solution.

In the context of the present invention, the $NO_x$ may preferably be adjusted content by a selective catalytic reduction with ammonia in which $N_2O$ behaves inertly. This technology, known as SCR-DeNOx or DeNOx technology, is described, for example, in Ullmann's Encyclopedia of Chemical Technology, Chapter "Air", Section 7.2.3.1. "Catalytic Reduction of Nitrogen Oxides in Flue Gases and Process Off-Gases", by J. Wolf et al., 6th edition (Online Edition), 2000. In this preferred embodiment of the present invention, it is possible to attain $NO_x$ concentrations of less than 100 ppm, preferably less than 50 ppm, for example less than 25 ppm, and more preferably of up to 5 ppm, and very low $NH_3$ concentrations in the product, for example less than 10 ppm.

In a preferred embodiment, as step C, the catalytic reduction with ammonia is carried out before steps A1, A2, B1 and B2.

In a particularly preferred embodiment of the present invention, the gas mixture which is used in the process according to the invention and comprises dinitrogen monoxide may stem from an adipic acid plant. The offgas of the adipic acid plant is preferably mixed with NO synthesis gas and cooled. The gaseous stream is then compressed, preferably to 7 bar, and, if appropriate, admixed with air. After the compression, the hot gas is cooled and passes into an absorption tower in which $NO_x$ is depleted. The gas at the top of the column preferably has a temperature of from about 0 to 100° C., for example from 20 to 50° C., preferably from 30 to 45° C., in particular from 35 to 40° C., at a pressure of from 1 to 15 bar, preferably from 4 to 14 bar, more preferably from 5 to 13 bar, in particular from 6 to 12 bar.

The offgas may be used directly in the process according to the invention. In a further preferred embodiment, however, the offgas may be heated to from 100 to 250° C., preferably from 150 to 200° C., more preferably to from 160 to 180° C., more preferably to 170° C., and be conducted into the DeNOx plant for the reaction in step C.

Subsequently, the stream is preferably cooled, compressed and cooled again before an absorption/desorption in step A1 and A2 and B1 and B2 is carried out. When an $NO_x$ concentration of <1% by volume is present in the $N_2O$-containing gas mixture, as, for example, in an offgas of a nitric acid plant, the absorbent used for step C is preferably an alkaline solution. In the context of the present invention, this procedure is preferably used for the fine purification of the $N_2O$ gas after the concentration in step A1, A2, B1 and B2.

In addition to steps A1, A2, B1 and B2 or, if appropriate, C, the process according to the invention may also comprise further steps. For example, the process may also comprise a further treatment between steps A and B and step C. Such treatments comprise, for example, a change in the temperature or a change in the pressure or a change in the temperature and in the pressure.

For example, the composition of a gas mixture may change, for example by condensation of one of the components. These components may, for example, be water or another solvent, preferably a solvent which is used for the absorption in step A1 in the process according to the invention.

According to the invention, it is possible that further components are removed from the gas mixture. For example, it is possible that traces of water which may be present in the gas mixture G-2 after the desorption in B2 may be removed from the gas mixture G-2 by compression and subsequent cooling.

In this case, the gas mixture G-2 is advantageously compressed to a pressure of from 1 to 35 bar, preferably from 2 to 30 bar, further preferably from 3 to 27 bar. Cooling is preferably effected subsequently, preferably to from 2 to 25° C., more preferably from 3 to 20° C., in particular from 4 to 15° C., further preferably from 5 to 10° C.

It is equally possible in the context of the present invention, for example, to carry out a partial condensation of dinitrogen monoxide or a rectification, especially to remove the low boilers, for example oxygen and nitrogen.

According to the invention, the gas mixture G-2 which comprises dinitrogen monoxide and has been purified by the process according to the invention can be used in a further reaction. To this end, the gas mixture may be used in gaseous form. However, it is also possible first to treat the resulting gas mixture such that the gas mixture is present in liquid or supercritical form and is then used in a further reaction. The gas mixture can be liquefied by suitable selection of the pressure or of the temperature.

The present invention thus also relates to a process, wherein the resulting gas mixture G-2 is liquefied.

To this end, the gas mixture G-2 is first preferably compressed and then cooled. In this case, the gas mixture G-2 is compressed advantageously to a pressure of from 1 to 35 bar, preferably from 2 to 30 bar, more preferably from 3 to 27 bar. Cooling is preferably effected subsequently, preferably to from 10 to −70° C., more preferably from 8 to −30° C., in particular from 5 to −20° C.

The gas mixture G-2 which comprises dinitrogen monoxide and has been obtained by a process according to the invention can in principle be used for all applications in which pure dinitrogen monoxide streams or dinitrogen monoxide streams admixed with inert gas are typically used. In particular, the gas mixtures are suitable, for example, for the oxidation of methanol to formaldehyde, as described, for example, in EP-A 0 624 565 or DE-A 196 05 211. The present invention therefore also relates to the use of the gas mixtures which comprise dinitrogen monoxide and are obtainable by a process according to the invention as an oxidizing agent for methanol.

The process according to the invention affords gas mixtures G-2 comprising dinitrogen monoxide which comprise a particularly low proportion of troublesome secondary components. This is advantageous especially for the use of the gas mixture comprising dinitrogen monoxide as the oxidizing agent, since, as a result of the low proportion of troublesome secondary components, hardly any side reactions occur and thus particularly pure products can be obtained. After the inventive purification, the gas mixture G-2 preferably also comprises carbon dioxide in addition to dinitrogen monoxide.

The gas mixture G-2 purified in accordance with the invention comprises preferably from 50 to 99.9% by volume of dinitrogen monoxide, from 0.1 to 25% by volume of carbon dioxide and from 0 to 25% by volume of further gases. The percentages by volume reported are each based on the overall gas mixture G-2. The sum of the individual components of the gas mixture G-2 always adds up to 100% by volume.

The gas mixture G-2 purified in accordance with the invention preferably comprises from 65 to 95% by volume of dinitrogen monoxide, in particular from 75 to 92.5% by volume, more preferably from 85 to 90% by volume of dinitrogen monoxide.

The gas mixture G-2 purified in accordance with the invention also comprises from 0.1 to 25% by volume of carbon dioxide. The gas mixture G-2 preferably comprises from 1 to 20% by volume of carbon dioxide, in particular from 2 to 15% by volume, more preferably from 5 to 13% by volume of carbon dioxide.

The gas mixture G-2 preferably comprises from 0.01 to 20% by volume of further gases, for example from 0.1 to 15% by volume, in particular from 0.5 to 10% by volume, more preferably from 1 to 5% by volume of further gases. The gas mixture G-2 purified in accordance with the invention may comprise one or more further gases, the amount specified being based on the sum of the gases present.

It has been found that, in the presence of $CO_2$ as an inert gas in gas mixtures comprising $N_2O$, distinctly smaller amounts of carbon dioxide in comparison to other inert gases are required in order to ensure safe operation, for example in order to suppress self-decomposition of dinitrogen monoxide.

One advantage of the process according to the invention is that $CO_2$, in addition to the good inertizing action in comparison to other inert gases, has a boiling curve very similar to that of $N_2O$ and similar critical parameters. As a result, the gas mixture G-2 which comprises $N_2O$ and, if appropriate, $CO_2$ and is obtained in the process according to the invention can be condensed at a higher temperature than a comparable mixture of $N_2O$ and another inert gas. As a result of the very similar boiling curves, the condensed gas mixture has almost the same composition as the gaseous mixture, so that the inertizing agent is retained in the liquid phase.

Moreover, $CO_2$ has a good solubility in organic compounds, so that a relatively low pressure is sufficient to avoid the formation of a gas phase in the reactor in the case of a reaction in the liquid phase.

The present invention therefore also relates to the use of a gas mixture obtainable by a process according to the invention, as described above, as an oxidizing agent, especially as an oxidizing agent for olefins.

In particular, the present invention also relates to the use of a gas mixture comprising from 50 to 99.9% by volume of dinitrogen monoxide, from 0.1 to 25% by volume of carbon dioxide and from 0 to 25% by volume of further gases as an oxidizing agent, especially as an oxidizing agent for olefins.

Such gas mixtures are obtainable, for example, by the purifying process according to the invention.

In principle, the gas mixtures which comprise dinitrogen monoxide and are obtainable in accordance with the invention are suitable for the oxidation of olefins. Suitable olefins are, for example, open-chain or cyclic olefins having one or more double bonds. Preference is further given to cyclic olefins having one or more double bonds, for example cyclopentene, cyclohexene, cycloheptene, cyclooctene, cyclodecene, cycloundecene, cyclododecene, 1,4-cyclohexadiene, 1,5-cyclooctadiene, 1,5-cyclododecadiene or 1,5,9-cyclododecatriene.

In a preferred embodiment, the present invention therefore also relates to a use as described above as an oxidizing agent for olefins, wherein the olefin is selected from the group consisting of cyclopentene, cyclododecene and 1,5,9-cyclododecatriene.

This enriched and purified $N_2O$-containing gas stream G-2 is suitable very particularly for the oxidation of olefins to ketones. For this purpose, it is possible with preference either to absorb the gaseous $N_2O$ directly into the olefin to be oxidized or another solvent, or the $N_2O$ can first be liquefied before it is reacted with the olefin.

Especially in the case of use of a liquefied gas mixture comprising dinitrogen monoxide, it is advantageous when the proportion of inert gases in the gas mixture is at a minimum, since the reactor volume is otherwise enlarged unnecessarily.

For the inventive use as an oxidizing agent, especially for olefins, the oxidation can generally be effected according to all process versions in which the oxidation, especially of the olefin, takes place. In particular, both continuous process versions and modes of reaction, and batchwise reaction are possible. According to the invention, the reaction conditions for the oxidation are selected such that a reaction takes place. Pressure and temperature can be selected appropriately.

The pressure is preferably in the range up to 350 bar, for example from 1 to 320 bar, preferably from 2 to 300 bar, in particular from 3 to 280 bar. The temperature is preferably in a range from 220 to 320° C., for example from 230 to 300° C., in particular from 250 to 290° C.

The oxidation may be carried out in the presence of a suitable solvent. However, it is equally possible in accordance with the invention to carry out the oxidation without the addition of a solvent.

However, it is also possible in the context of the present invention that the gas mixture G-2 is liquefied or brought into a supercritical state by a suitable selection of the pressure and/or of the temperature. The liquefied gas mixture can then be used directly in the oxidation.

According to the invention, the oxidation in this case is preferably conducted by a suitable selection of the pressure and of the temperature such that no gas phase occurs in the reaction zone.

The pressure is preferably in the range up to 350 bar, for example from 1 to 320 bar, preferably from 2 to 300 bar, in particular from 3 to 280 bar. The temperature is preferably in a range from 220 to 320° C., for example from 230 to 300° C., in particular from 250 to 290° C.

The present invention therefore also relates to a process for preparing a ketone, at least comprising the following steps
- A1 absorption of a gas mixture G-0 comprising dinitrogen monoxide in an organic solvent
- A2 desorption of a gas mixture G-1 from the laden organic solvent
- B1 absorption of the gas mixture G-1 in water
- B2 desorption of a gas mixture G-2 from the laden water
- D contacting the gas mixture G-2 with at least one olefin.

As described above, the process may also comprise at least one step C.

For the preferred embodiments of steps A1, A2 and B1 and B2, the above remarks apply. For the preparation of a ketone too, the sequence of steps A1, A2, B1 and B2 on the one hand and C on the other may vary. According to the invention, step C may be performed after steps A1, A2, B1 and B2. However, it is equally possible that step C is performed before steps A1, A2, B1 and B2. In every case, however, step D is carried out after steps A1, A2, B1 and B2.

In principle, it is possible to perform step C before steps A1, A2, B1 and B2. However, it is equally possible in the context of the present invention that step C is performed after steps A1, A2, B1 and B2. In a further embodiment, the present invention therefore also relates to a process for preparing a ketone as described above, in which steps A1, A2, B1 and B2 are performed before step C. In an alternative embodiment, the present invention also relates to a process for preparing a ketone in which step C is performed before steps A1, A2, B1 and B2.

It is equally possible in the context of the present invention that the process comprises a plurality of steps A1 and A2 or a plurality of steps B1 and B2 or a plurality of steps C, in which case step C may be carried out before or after steps A1, A2, B1 and B2.

The reaction in step D may generally be effected according to any process versions in which the olefin and the gas mixture G-2 comprising dinitrogen monoxide react with one another. In particular, both continuous process versions and modes of reaction, and batchwise reaction are possible. According to the invention, the reaction conditions for step D are selected in such a way that a reaction of the at least one olefin with the gas mixture purified in accordance with the invention takes place. Pressure and temperature may be selected appropriately.

The reaction may be carried out in the presence of a suitable solvent. However, it is equally possible in accordance with the invention to carry out the reaction in step D without the addition of a solvent.

However, it is also possible in accordance with the invention that the process for preparing a ketone comprises further steps. For instance, the gas mixture comprising dinitrogen monoxide may be treated, for example, before step D and after steps A1, A2, B1 and B2. A possible treatment is, for example, a change in pressure and/or temperature of the gas mixture. A further possible treatment is, for example, absorption in a solvent, so that the absorbed gas mixture may be used in step D. The solvent may be any suitable solvent. The solvent is preferably the olefin which is to be oxidized in step D.

However, it is also possible in the context of the present invention that the gas mixture G-2 comprising dinitrogen monoxide is liquefied by suitable selection of the pressure and/or the temperature or is brought into a supercritical state before step D and after steps A1, A2, B1 and B2. The liquefied gas mixture comprising dinitrogen monoxide may then be contacted directly with the olefin in step D.

The present invention therefore also relates in a further embodiment to a process for preparing a ketone as described above, wherein the gas mixture used in step D has been liquefied.

In principle, it is possible in step D of the process according to the invention to use all suitable olefins, for example olefins having from 2 to 18 carbon atoms, in particular olefins having from 5 to 12 carbon atoms. Suitable olefins are, for example, open-chain or cyclic olefins having one or more double bonds. Preference is further given to cyclic olefins having one or more double bonds, for example cyclopentene, cyclohexene, cycloheptene, cyclooctene, cyclodecene, cycloundecene, cyclododecene, 1,4-cyclohexadiene, 1,5-cyclooctadiene, 1,5-cyclododecadiene or 1,5,9-cyclododecatriene.

Particular preference is given to using as the olefin cyclopentene, cyclododecene or 1,5,9-cyclododecatriene. In a preferred embodiment, the present invention therefore relates to a process for preparing a ketone as described above, wherein the olefin is selected from the group consisting of cyclopentene, cyclododecene and 1,5,9-cyclododecatriene.

The invention will be illustrated hereinafter with reference to examples.

EXAMPLES

Example 1

Comparative Example, Double Absorption/Desorption in Nitrobenzene

The offgas of a nitric acid plant which is operated with the offgas from an adipic acid plant and comprises about 1500 ppm by volume of $NO_x$ is first freed of nitrogen oxides in a DeNOx stage.

The gas mixture G-0 thus obtained (2 kg/h) is compressed to 25 bar and absorbed in nitrobenzene at 35° C. in an absorption column A1 (diameter=80 mm, height=1800 mm, filled with a wire mesh packing (Kühni Rombopak 9M)). The $N_2O$-laden nitrobenzene from A1 is then decompressed to 1.1 bar to a flash vessel A2, likewise at 35° C. In the circuit through A1 and A2, 200 kg/h of nitrobenzene are circulated.

The gas mixture G-1 obtained from the first desorber is compressed again to 25 bar and absorbed in nitrobenzene at 35° C. in a second absorption column B1 (diameter=30 mm, height=1800 mm, filled with a wire mesh packing (Kühni Rombopak 9M)). The $N_2O$-laden nitrobenzene from B1 is then decompressed to 1.1 bar to a flash vessel B2, likewise at 35° C. This results in gas mixture G-2. In the circuit through B1 and B2, 25 kg/h of nitrobenzene are circulated.

| Component | G-0 [% by vol.] | G-1 [% by vol.] | G-2 [% by vol.] |
|---|---|---|---|
| $N_2O$ | 8.1 | 57.2 | 86.5 |
| $N_2$ | 86.5 | 30.2 | 1.9 |
| $CO_2$ | 1.1 | 7.1 | 10.5 |
| $H_2O$ | 0.3 | 2.6 | 0.7 |
| $O_2$ | 3.1 | 1.9 | 0.2 |
| $NO_x$ | 13 vppm | 32 vppm | 50 vppm |

Owing to the high concentration of $N_2O$ in the gas phase in apparatuses B1 and B2 and the presence of the combustible organic solvent nitrobenzene, these apparatuses are critical from a safety point of view. In order to ensure safe operation of stages B1 and B2, these would have to be designed so as to be resistant to pressure surges at 1000 bar in order to survive ignition, which cannot be ruled out, undamaged.

Example 2

Absorption/Desorption in Nitrobenzene and Absorption/Desorption in Water

The offgas of a nitric acid plant which is operated with the offgas from an adipic acid plant and comprises about 1500 ppm by volume of $NO_x$ is first freed of nitrogen oxides in a DeNOx stage.

The gas mixture G-0 thus obtained (2 kg/h) is compressed to 25 bar and absorbed in nitrobenzene at 35° C. in the same absorption column as in Example 1. As above, the desorption is effected at 1.1 bar and 35° C. in order to generate an identical gas mixture G-1.

As above, the gas mixture G-1 is compressed to 25 bar and absorbed in water at 35° C. in an absorption column B1 (diameter=70 mm, height=1800 mm, filled with a wire mesh packing). In the circuit through B1 and B2, 112 kg/h of water are circulated. The $N_2O$-laden water from B1 is then decompressed to 1.1 bar in a flash vessel B2, likewise at 35° C. This results in gas mixture G-2.

| Component | G-0 [% by vol.] | G-1 [% by vol.] | G-2 [% by vol.] |
|---|---|---|---|
| $N_2O$ | 8.1 | 58.0 | 81.6 |
| $N_2$ | 86.5 | 29.3 | 2.0 |
| $CO_2$ | 1.1 | 7.3 | 10.7 |
| $H_2O$ | 0.3 | 2.4 | 5.3 |
| $O_2$ | 3.1 | 1.9 | 0.3 |
| $NO_x$ | 13 vppm | 21 vppm | 30 vppm |

When the water content is disregarded, the gas mixture G-2 has a very similar composition to that in Example 1. Since, though, no organic solvent is present in the second absorption/desorption stage, stages B1 and B2 are easily controllable from a safety point of view. It is sufficient to design the plants for maximum pressure 30 bar.

The process according to the invention thus offers a distinct economic advantage in the form of lower capital costs and lower expenditures for safety technology.

What is claimed is:

1. A process for purifying a gas mixture G-0 comprising dinitrogen monoxide, said process comprising at least the following steps:
    A1 absorption of the gas mixture G-0 in an organic solvent;
    A2 desorption of a gas mixture G-1 from the laden organic solvent;
    B1 absorption of the gas mixture G-1 in water; and
    B2 desorption of a gas mixture G-2 from the laden water.

2. The process according to claim 1, wherein said gas mixture G-0 comprising dinitrogen monoxide is the offgas of an adipic acid plant and/or of a dodecanedicarboxylic acid plant and/or of a hydroxylamine plant and/or of a nitric acid plant operated with the offgas of an adipic acid plant and/or of a dodecanedicarboxylic acid plant and/or of a hydroxylamine plant.

3. The process according to claim 1, wherein the organic solvent is selected from the group consisting of toluene, nitrobenzene, 1,2-dichlorobenzene, tetradecane and dimethyl phthalate.

4. The process according to claim 1, wherein the pressure in the absorption in A1 or B1 is in a range of from 10 to 35 bar.

5. The process according to claim 1, wherein steps A1 and A2 or steps B1 and B2 or steps A1 and A2 and steps B1 and B2 are carried out in a dividing wall column.

6. The process according to claim 1, which additionally comprises the step of
    C adjusting the content of nitrogen oxides $NO_x$ in the gas mixture to at most 0.5% by volume based on the total volume of the gas mixture.

7. The process according to claim 6, wherein step C is performed before steps A1, A2, B1 and B2.

8. The process according to claim 1, wherein the resulting gas mixture G-2 is liquefied.

9. A process for purifying a gas mixture G-0 comprising dinitrogen monoxide, said process comprising the following steps:
    A1 absorption of the gas mixture G-0 in an organic solvent;
    A2 desorption of a gas mixture G-1 from the laden organic solvent;
    B1 absorption of the gas mixture G-1 in water; and
    B2 desorption of a gas mixture G-2 from the laden water, wherein the process additionally comprises the step of
    C adjusting the content of nitrogen oxides $NO_x$ in the gas mixture to at most 0.5% by volume based on the total volume of the gas mixture.

10. The process according to claim 9, wherein the organic solvent is selected from the group consisting of toluene, nitrobenzene, 1,2-dichlorobenzene, tetradecane and dimethyl phthalate.

11. The process according to claim 9, wherein the resulting gas mixture G-2 is liquefied.

12. The process according to claim 9, wherein step C is performed before steps A1, A2, B1 and B2.

13. A process for purifying a gas mixture G-0 comprising dinitrogen monoxide, said process comprising at least the following steps:
    A1 absorption of the gas mixture G-0 in an organic solvent at a pressure of 10 to 35 bar;
    A2 desorption of a gas mixture G-1 from the laden organic solvent at a pressure of 0.5 to 1.5 bar;
    B1 absorption of the gas mixture G-1 in water at a pressure of 10 to 35 bar; and B2 desorption of a gas mixture G-2 from the laden water at a pressure of 0.5 to 1.5 bar;

wherein said process additionally comprises step C of adjusting the content of nitrogen oxides $NO_x$ in the gas mixture to at most 0.5% by volume based on the total volume of the gas mixture.

14. The process according to claim 13, wherein the pressure in absorption steps A1 and B1 is in a range of from 15 to 30 bar.

15. The process according to claim 13, wherein the pressure in absorption steps A1 and B1 is in a range of from 16 to 25 bar.

16. The process according to claim 13, wherein said process additionally comprises step C of adjusting the content of nitrogen oxides $NO_x$ in the gas mixture to at most 0.5% by volume before steps A1, A2, B1 and B2, and after the first absorption/desorption in A1 and A2 and before the second absorption/desorption in B1 and B2, the gas mixture has an $N_2O$ content of from 50 to 75% by volume.

17. The process according to claim 16, wherein after the second absorption/desorption in B1 and B2, the gas mixture has an $N_2O$ content of from 75 to 85% by volume.

18. The process according to claim 13, wherein said process additionally comprises step C of adjusting the content of nitrogen oxides $NO_x$ in the gas mixture to at most 0.5% by volume after steps A1, A2, B1 and B2, and after the first absorption/desorption in A1 and A2 and before the second absorption/desorption in B1 and B2, the gas mixture has an $N_2O$ content of from 50 to 75% by volume.

19. The process according to claim 18, wherein after the second absorption/desorption in B1 and B2 and step C, the gas mixture has an $N_2O$ content of from 75 to 85% by volume.

* * * * *